US012725534B2

(12) United States Patent
Huang et al.

(10) Patent No.: US 12,725,534 B2
(45) Date of Patent: Sep. 1, 2026

(54) SYSTEM AND OPERATION METHOD

(71) Applicant: THE UNIVERSITY OF TOKYO, Tokyo (JP)

(72) Inventors: Shouren Huang, Tokyo (JP); Yuji Yamakawa, Tokyo (JP); Masatoshi Ishikawa, Tokyo (JP)

(73) Assignee: THE UNIVERSITY OF TOKYO (JP)

( * ) Notice: Subject to any disclaimer, the term of this patent is extended or adjusted under 35 U.S.C. 154(b) by 768 days.

(21) Appl. No.: 17/924,379

(22) PCT Filed: May 25, 2021

(86) PCT No.: PCT/JP2021/019754
§ 371 (c)(1),
(2) Date: Nov. 10, 2022

(87) PCT Pub. No.: WO2021/241558
PCT Pub. Date: Dec. 2, 2021

(65) Prior Publication Data

US 2023/0186784 A1 Jun. 15, 2023

(30) Foreign Application Priority Data

May 26, 2020 (JP) ................................ 2020-091522

(51) Int. Cl.
*G09B 19/00* (2006.01)
*G09B 19/24* (2006.01)
(Continued)

(52) U.S. Cl.
CPC ........... *G09B 19/003* (2013.01); *G09B 19/24* (2013.01); *A61B 5/02438* (2013.01); *A61B 5/681* (2013.01);
(Continued)

(58) Field of Classification Search
CPC .......... G06F 3/011; G06F 3/016; G06F 3/014; A61B 5/02438; A61B 5/681;
(Continued)

(56) References Cited

U.S. PATENT DOCUMENTS 5,873,788 A * 2/1999 Hoffman ............ A63B 69/0059 2/161.2
9,104,271 B1 * 8/2015 Adams .................. G06F 3/0233
(Continued)

FOREIGN PATENT DOCUMENTS

JP 2009-244428 A 10/2009
JP 2011-059219 A 3/2011
(Continued)

OTHER PUBLICATIONS

International Search Report (English and Japanese) issued in PCT/JP2021/019754, mailed Aug. 24, 2021; ISA/JP (5 pages).

*Primary Examiner* — Jack Yip
(74) *Attorney, Agent, or Firm* — Harness, Dickey & Pierce, P.L.C.

(57) ABSTRACT

A system is provided that effectively assists a user in learning a prescribed motion, irrespective of the user's age and motivation. The system comprises a first contact unit, a sensor unit, and a second contact unit. The first contact unit is connected to a point to be operated. By the first contact unit coming into contact with a first limb of a user, a target position that is defined by the point to be operated is variably configured in conformity with the motion of the first limb. The sensor unit is configured so as to measure an error from the prescribed trajectory of the target position. The second contact unit is provided with an error sensation presentation unit and is configured so as to come into contact with a second limb that is different from the first limb of the user. The error sensation presentation unit is configured so as to
(Continued)

add a kinesthetic or tactile sense based on the error to the second limb and thereby present the error to the user.

9 Claims, 8 Drawing Sheets

(51) Int. Cl.
*A61B 5/00* (2006.01)
*A61B 5/024* (2006.01)
*A63B 71/06* (2006.01)
*G06F 3/01* (2006.01)

(52) U.S. Cl.
CPC ....... *A63B 2071/0655* (2013.01); *G06F 3/011* (2013.01); *G06F 3/014* (2013.01); *G06F 3/016* (2013.01); *G09B 19/0038* (2013.01)

(58) Field of Classification Search
CPC .......... A63B 2071/0655; G09B 19/003; G09B 19/0038; G09B 19/24
See application file for complete search history.

(56) References Cited

U.S. PATENT DOCUMENTS

2007/0120979 A1* 5/2007 Zhang .................... H04N 7/185 348/154
2009/0151483 A1* 6/2009 Kim ..................... B62D 55/116 74/2
2013/0162852 A1* 6/2013 Boyle ................ H04N 23/6812 348/211.99
2014/0221116 A1* 8/2014 Coucher ................ A63B 59/50 473/409
2014/0248594 A1* 9/2014 Navas ................ G09B 19/0038 434/247
2015/0310762 A1* 10/2015 Seim ...................... G09B 15/00 434/113
2016/0363997 A1* 12/2016 Black ...................... G06F 3/014
2017/0128816 A1* 5/2017 DeMarch ............. G09B 19/003
2018/0296419 A1* 10/2018 Tong ...................... B25J 9/0006
2018/0315247 A1* 11/2018 Van Andel ............. G06F 3/017
2018/0369367 A1 12/2018 McKenna
2019/0087002 A1* 3/2019 Mani ....................... G06T 7/246
2019/0311648 A1* 10/2019 Alshami .................. G09B 5/04
2019/0346925 A1* 11/2019 Daniels ................... G06F 3/012
2020/0138363 A1* 5/2020 McCarthy .............. A61B 5/486
2021/0299870 A1* 9/2021 Huang ..................... B25J 13/00

FOREIGN PATENT DOCUMENTS

JP 2017-023223 A 2/2017
JP 2017-134116 A 8/2017
JP 2020-012858 A 1/2020

* cited by examiner

CONTROL APPARATUS

2

IM

CS

4

IMAGING APPARATUS

MAIN APPARATUS

FIG. 3

3
31
32
COMMUNICATION UNIT
STORAGE UNIT
CONTROLLER
30
33

IMAGING APPARATUS 2
CONTROL APPARATUS 3
MAIN APPARATUS 4
A101
GRASP WITH BOTH HANDS
A102
OPERATE WITH RIGHT HAND RH
A103
IMAGE OPERATION MODE
A104
SPECIFY LINE L
A105
CALCULATE ERROR VECTOR v1
A106
CORRECT ERROR E
[IN SECOND RANGE]
[OUT OF SECOND RANGE]
A107
PRESENT ERROR E
[NEXT]
[END]

SYSTEM AND OPERATION METHOD

CROSS REFERENCE TO RELATED APPLICATIONS

This application is a U.S. National Phase Application under 35 U.S.C. 371 of International Application No. PCT/JP2021/019754, filed on May 25, 2021, which claims priority to Japanese Patent Application No. 2020-091522, filed on May 26, 2020. The entire disclosures of the above applications are expressly incorporated by reference herein.

BACKGROUND

Technical Field

The present invention relates to a system and an operation method.

Related Art

There are many situations in which human perform a task involving a predetermined action with his/her limb. Patent Application Publication No. 2020-12858 discloses a skill training apparatus used to train such a predetermined action.

The skill training apparatus disclosed in Patent Application Publication No. 2020-12858 reports information when a user performs an action different from the predetermined action, thus the user needs to consciously read the information. Therefore, learning effect decreases depending on age or motivation of the user.

In view of the above circumstances, the present invention provides a technology for assisting a user to effectively learn a predetermined action regardless of age or motivation of the user.

SUMMARY

According to an aspect of the present invention, a system is provided. The system comprising: a first contact unit connecting to an operated portion, and configured to change a target position defined by the operated portion in accordance with a movement of a first limb by contacting the first limb of a user; a sensor unit configured to measure an error of the target position from a predetermined trajectory; and a second contact unit including an error sense presentation unit, and configured to contact a second limb of the user that is different from the first limb; wherein the error sense presentation unit is configured to present the error to the user by imparting a force sense or a tactile sense based on the error to the second limb.

Thereby, a user can effectively learn a predetermined action regardless of age or motivation of the user.

BRIEF DESCRIPTION OF THE DRAWINGS

FIG. 2 is a schematic diagram showing an overall configuration of the system 1.

FIG. 3 is a block diagram showing a hardware configuration of a control apparatus 3.

DETAILED DESCRIPTION

Hereinafter, embodiment of the present invention will be described with reference to the drawings. Various features described in the embodiment below can be combined with each other.

A program for realizing a software in the present embodiment may be provided as a non-transitory computer readable medium that can be read by a computer or may be provided for download from an external server or may be provided so that the program can be activated on an external computer to realize functions thereof on a client terminal (so-called cloud computing).

In the present embodiment, the "unit" may include, for instance, a combination of hardware resources implemented by a circuit in a broad sense and information processing of software that can be concretely realized by these hardware resources. Further, various information is performed in the present embodiment, and the information can be represented by, for instance, physical values of signal values representing voltage and current, high and low signal values as a set of binary bits consisting of 0 or 1, or quantum superposition (so-called qubits), and communication/calculation can be performed on a circuit in a broad sense.

Further, the circuit in a broad sense is a circuit realized by combining at least an appropriate number of a circuit, a circuitry, a processor, a memory, and the like. In other words, it is a circuit includes application specific integrated circuit (ASIC), programmable logic device (e.g., simple programmable logic device (SPLD), complex programmable logic device (CPLD), and field programmable gate array (FPGA)), and the like.

1. Hardware Configuration

In this section, a hardware configuration of a system 1 according to an embodiment will be described.

1.1 System 1

Figure 1:
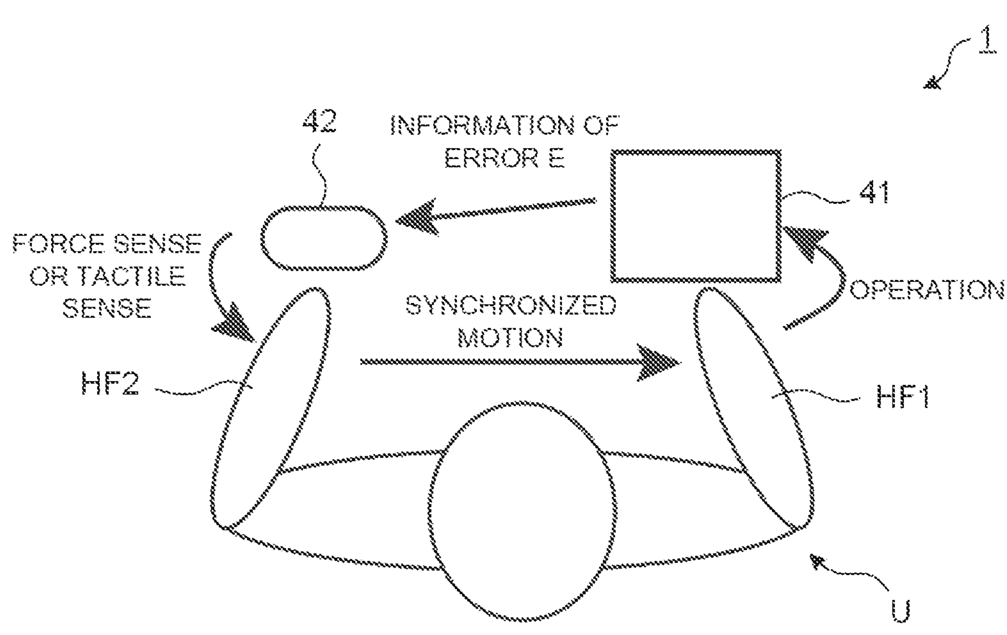
FIG. 1 is a schematic diagram showing an overall configuration of a system 1.
Figure 2:
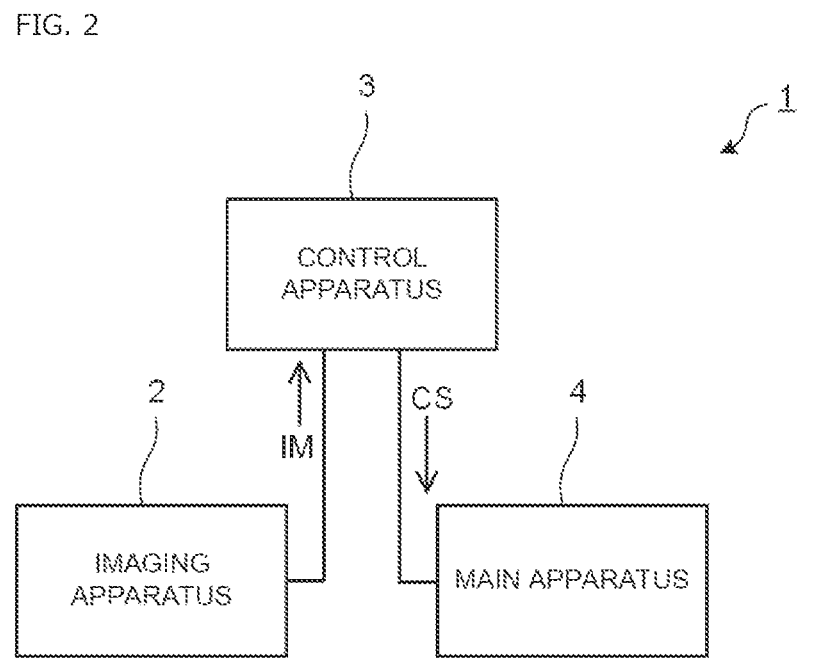

FIGS. 1 and 2 are schematic diagrams showing an overall configuration of the system 1. As shown in FIG. 1, a user U can use the system 1 to perform training of a predetermined action. Here, the training may be training for a healthy user U to learn a predetermined action, or training for an injured user U for a purpose of rehabilitation. As shown in FIG. 2, the system 1 comprises an imaging apparatus 2 (an example of a sensor unit), a control apparatus 3, and a main apparatus 4, which are electrically connected.

1.2 Imaging Apparatus 2

The imaging apparatus 2 is a so-called vision sensor (camera) configured to image information of an external world, and it is especially preferable to use a high frame rate, referred to as high-speed vision.

The imaging apparatus 2 (sensor unit) is configured to measure an error E of a target position TP from a predetermined trajectory. This will be described in more detail later. Preferably, frame rate (acquisition rate) of the imaging apparatus 2 (sensor unit) is 100 fps (Hz) or more, and more specifically, for instance, may be 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1025, 1050, 1075, 1100, 1125, 1150, 1175, 1200, 1225, 1250, 1275, 1300, 1325, 1350, 1375, 1400, 1425, 1450, 1475, 1500, 1525, 1550, 1575, 1600, 1625, 1650, 1675, 1700, 1725, 1750, 1775, 1800, 1825, 1850, 1875, 1900, 1925, 1950, 1975, 2000 fps, or may be in a range between any two of the numerical values exemplified above.

The imaging apparatus 2 is connected to a communication unit 31 of the control apparatus 3 described later via an electric communication line (e.g., a USB cable, etc.), and is configured to transfer a captured image IM to the control apparatus 3.

In addition, in the imaging apparatus 2, a camera capable of measuring not only visible light but also bands such as an ultraviolet range or an infrared range that human cannot perceive may be employed. By adopting such a camera, the system 1 according to the present embodiment can be implemented even in a dark field.

1.3 Control Apparatus 3

Figure 3:
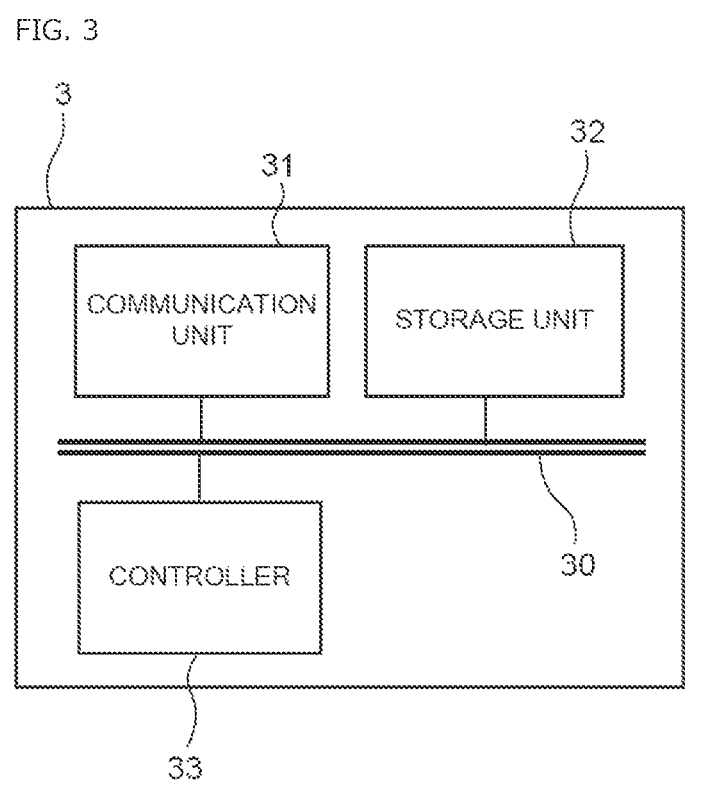

FIG. 3 is a block diagram showing a hardware configuration of the control apparatus 3. As shown in FIG. 3, the control apparatus 3 comprises a communication unit 31, a storage unit 32, and a controller 33, and these components are electrically connected inside the control apparatus 3 via a communication bus 30. Hereinafter, each component will be further described.

The communication unit 31 preferably uses wired communication means such as USB, IEEE 1394, Thunderbolt, wired LAN network communication, etc., but wireless LAN network communication, mobile communication such as 3G/LTE/5G, Bluetooth (registered trademark) communication, etc. may be included as necessary. In other words, it is preferable to implement a set of these multiple communication means. This allows information and command to be exchanged between the control apparatus 3 and other communicable apparatus.

The storage unit 32 stores various information defined by the above description. This may be implemented as, for example, a storage device such as a solid state drives (SSD), or a memory such as a random access memory (RAM) storing temporarily necessary information (argument, array, etc.) related to program operation, etc. Further, combination thereof may also be used. The storage unit 32 stores various programs that can be read by the controller 33 described later. Furthermore, the storage unit 32 stores time series of the image IM captured by the imaging apparatus 2 and received by the communication unit 31. Here, the image IM is, for example, sequence information including pixel information of 8 bits each of RGB.

The controller 33 performs process and control of overall operation related to the control apparatus 3. The controller 33 is, for example, an unshown central processing unit (CPU). The controller 33 reads out a predetermined program stored in the storage unit 32 to realize various functions related to the control apparatus 3. That is, information processing by software (stored in storage unit 32) is specifically realized by hardware (controller 33), and may be executed as each functional unit of the controller 33, as shown in FIG. 3. Note that although FIG. 3 shows a single controller 33, the present invention is not limited to this, and a plurality of controllers 33 may be provided for each function. Moreover, a combination thereof may be adopted.

1.4 Main Apparatus 4

Figure 4:
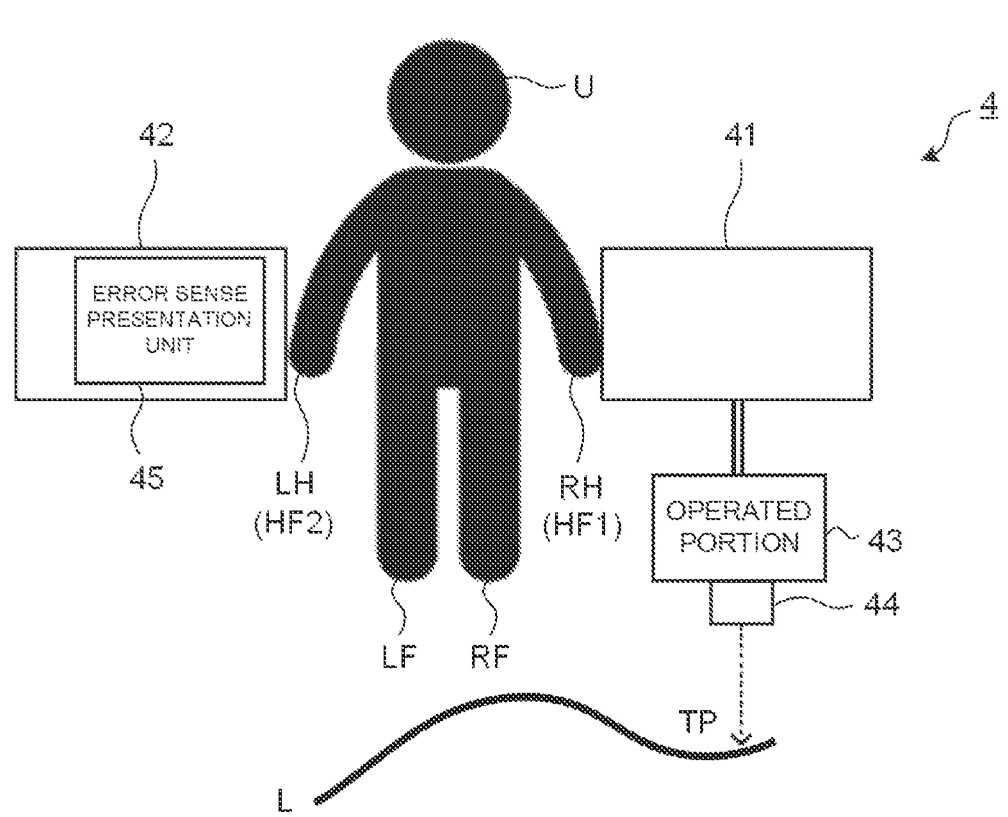
FIG. 4 is a schematic diagram showing a hardware configuration of a main apparatus 4.

FIG. 4 is a schematic diagram showing a hardware configuration of the main apparatus 4. The main apparatus 4 is an apparatus that allows a user U to operate an operated portion 43 using his/her own limb. Moreover, the main apparatus 4 is an apparatus that receives a control signal CS from the control apparatus 3 and drives in various ways accordingly. The main apparatus 4 comprises a first contact unit 41 and a second contact unit 42.

As shown in FIG. 4, the first contact unit 41 is connected to the operated portion 43. The first contact unit 41 is configured to change the target position TP defined by the operated portion 43 in accordance with a movement of a first limb HF1 by contacting the first limb HF1 of the user U. A range of the target position TP that can be moved by the user U using the first contact unit 41 shall be referred to as a first range.

As shown in FIG. 4, the second contact unit 42 includes an error sense presentation unit 45, and is configured to contact a second limb HF2 of the user U that is different from the first limb HF1. The error sense presentation unit 45 is configured to present the error E to the user U by imparting a force sense or a tactile sense based on the error E measured via the imaging apparatus 2 to the second limb HF2.

It should be noted that form of the first contact unit 41 and the second contact unit 42 is not particularly limited, but an appropriate form may be selected according to usability of contacting the first limb HF1 or the second limb HF2. For instance, if the first limb HF1 and the second limb HF2 are a left hand and a right hand (left hand LH and right hand RH) of the user U, then the first contact unit 41 and the second contact unit 42 may be configured to be graspable by the left hand LH and the right hand RH, respectively.

The main apparatus 4 further comprises a position adjustment unit 44. The position adjustment unit 44 is, for example, a stage that can be driven in an XY direction, and is preferably capable of displacing the operated portion 43 within a second range that is smaller than the first range that can be operated by the user U. With such a configuration, the position adjustment unit 44 can adjust the target position TP of the operated portion 43 so as to correct the error E.

As for the system 1 as a whole, a lower one of a frame rate of the imaging apparatus 2 and a drive rate of the position adjustment unit 44 functions as a control rate for correction of the error E. In other words, by setting the frame rate and the drive rate to the same high level, it is possible to correct the error E of the target position TP only by feedback control without using prediction at all. That is, preferably, the drive rate of the position adjustment unit 44 is 100 Hz or more, as is the case with the imaging apparatus 2.

It should be noted that in training of a predetermined action by the user U, the correction by the position adjustment unit 44 may not be performed. The correction by the position adjustment unit 44 is like camera-shake correction and assists in realizing an appropriate predetermined action. The user U may be trained to perform the predetermined action correctly even in a situation where the position adjustment unit 44 is not provided. Such a case would impose a more advanced operation by user U, but such training is not precluded.

2. Functional Configuration

Figure 5:
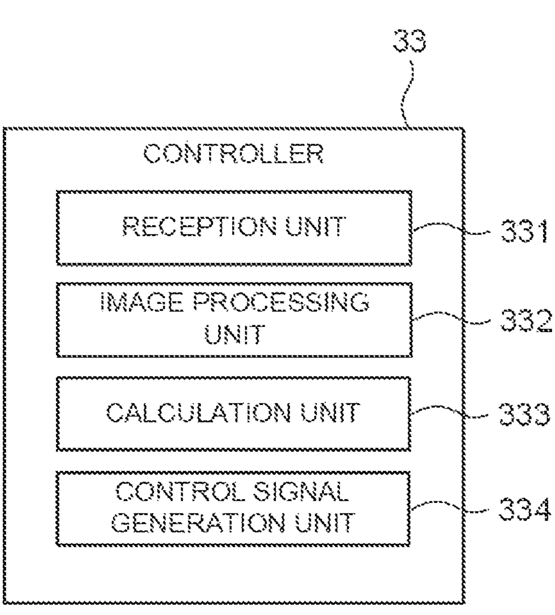
FIG. 5 is a block diagram showing a functional configuration of a control apparatus 3 (controller 33).

This section describes a functional configuration of the present embodiment. FIG. 5 is a block diagram showing a functional configuration of the control apparatus 3 (controller 33). With respect to the aforementioned controller 33, the control apparatus 3 comprises a reception unit 331, an image processing unit 332, a calculation unit 333, and a control signal generation unit 334. Hereinafter, each component will be further described.

Reception Unit 331

The reception unit 331 is configured to receive information via the communication unit 31 or the storage unit 32 and read it into a working memory. In particular, the reception unit 331 is configured to receive information (image IM, displacement information of the position adjustment unit 44, etc.) from the imaging apparatus 2 and/or the main apparatus 4 via the communication unit 31. If the control apparatus 3 is connected to other devices, the reception unit 331 may be implemented to receive information transmitted from those devices. In the present embodiment, various information received by the reception unit 331 is described as being stored in the storage unit 32.

After the reception unit 331 receives and temporarily reads into the working memory, at least part of the information may not be stored in the storage unit 32. Furthermore, at least part of the information may be stored in an external server other than the storage unit 32.

Image Processing Unit 332

The image processing unit 332 is configured to read a program stored in the storage unit 32 for the image IM and execute predetermined image processing. For example, the image processing unit 332 executes image processing for specifying a line L, which is a predetermined trajectory from the image IM. Details thereof will be described later.

Calculation Unit 333

The calculation unit 333 is configured to execute a predetermined calculation using the image IM that has undergone image processing by the image processing unit 332. For instance, the calculation unit 333 calculates an error vector v1 or a symmetry vector v2 from the image IM. Details thereof will be described later.

Control Signal Generation Unit 334

The control signal generation unit 334 is configured to generate the control signal CS for controlling the main apparatus 4. Specifically, the control signal generation unit 334 generates a control signal CS1 that allows the position adjustment unit 44 to drive. Moreover, the control signal generation unit 334 generates a control signal CS2 that allows the error sense presentation unit 45 to operate. Value of the control signal CS may be defined, for instance, in terms of voltage.

3. Control Processing

This section describes control process flow of the system 1.

3.1 Operation Method

Figure 6:
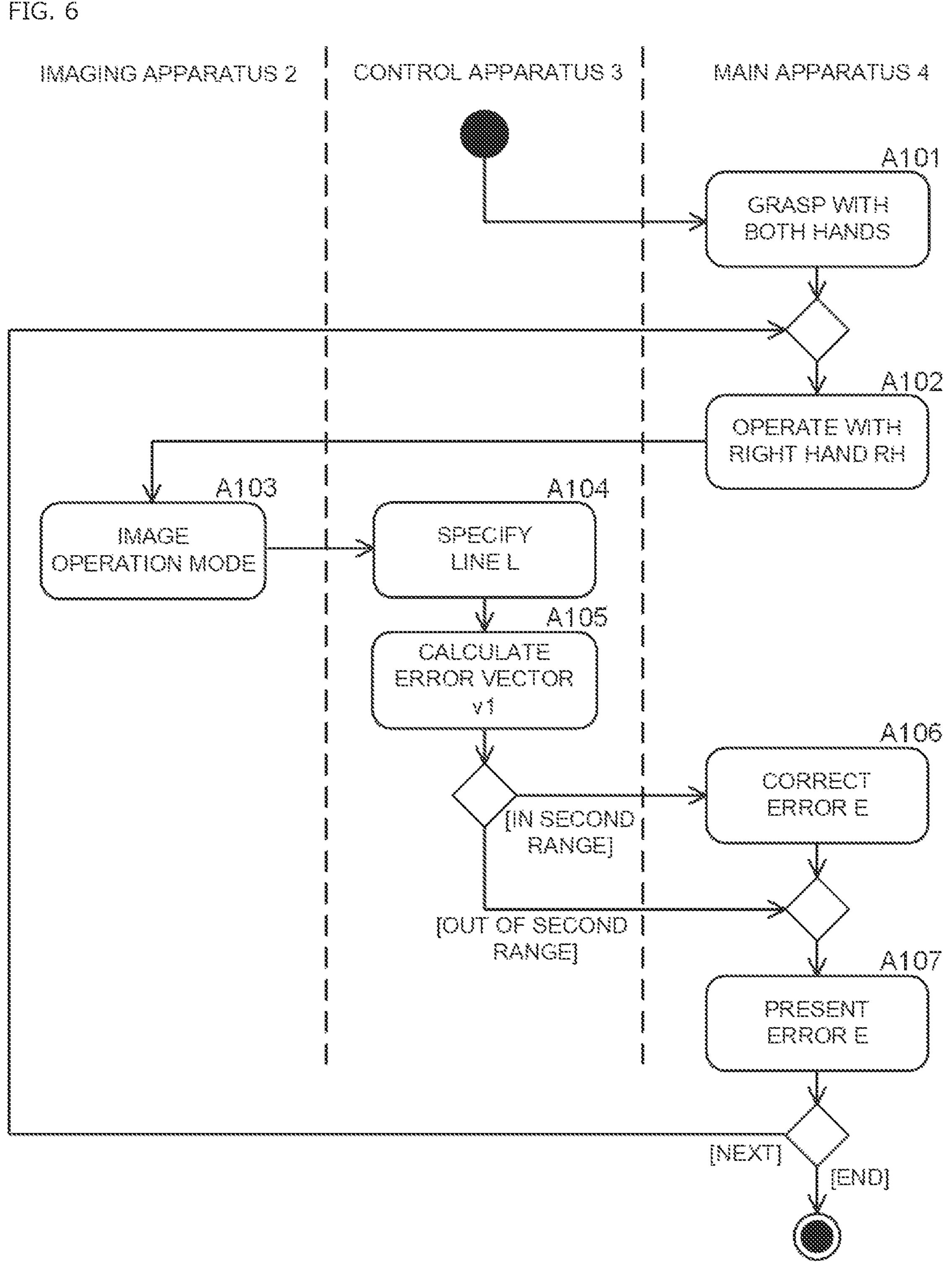
FIG. 6 is an activity diagram showing an operation method of the system 1.

FIG. 6 is an activity diagram showing an operation method of the system 1. Here, for simplicity, it is assumed that the user U is right-handed, the first limb HF1 is the right hand RH, and the second limb HF2 is the left hand LH. That is, the user U grasps the first contact unit 41 with the right hand RH, and grasps the second contact unit 42 with the left hand LH (Activity A101). Grasping is an example of contact. Then, the user U operates the first contact unit 41 with the right hand RH to allow the target position TP of the operated portion 43 to move along the line L, which is a predetermined trajectory (Activity A102). Such an operation is included in, for instance, cutting operation, application operation, medical operation, or the like.

When the user U allows the first contact unit 41 to displace, the target position TP is also displaced accordingly. At this time, the target position TP and the line L are captured by the imaging apparatus 2, and the image IM is transmitted to the control apparatus 3 (Activity A103). That is, the reception unit 331 receives the image IM, and the image IM is stored in the storage unit 32.

Figure 7:
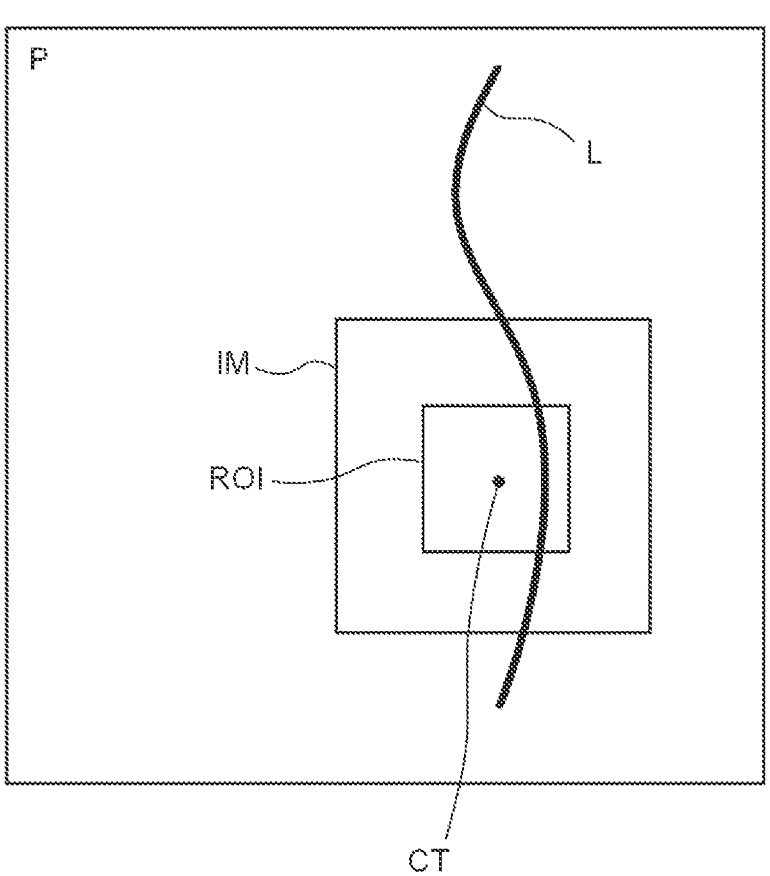
FIG. 7 is a schematic diagram showing an example of an image IM on which an image processing unit 332 performs image processing.

FIG. 7 is a schematic diagram showing an example of the image IM on which the image processing unit 332 performs image processing. The image processing unit 332 analyzes the image IM received by the reception unit 331 with image processing, and specify a position of the line L in the image IM (Activity A104). This is implemented, for example, by binarizing the captured image IM by determining a threshold value for a predetermined parameter (brightness, etc.) in relation to the image. The position of the line L can then be specified by calculating a center of gravity of the line L from the image IM.

Then, it is preferable that the target position TP is implemented as an intersection point between a line of sight of the imaging apparatus 2 and a regulation surface P. Although not shown in FIG. 4, the imaging apparatus 2 is attached to the position adjustment unit 44. In other words, the target position TP is a center of the image IM (image center CT) captured by the imaging apparatus 2.

As shown in FIG. 7, image processing may be performed on a predetermined region ROI that is part of the image IM. In particular, to correct the error E at a high control rate, the line L is in a vicinity of a fixed position (e.g., image center CT) in the image IM, and number of pixels for image processing can be reduced by setting a vicinity region of the fixed position as the predetermined region ROI. As a result, a calculation load on the control apparatus 3 can be reduced and a high control rate can be maintained.

Figure 8:
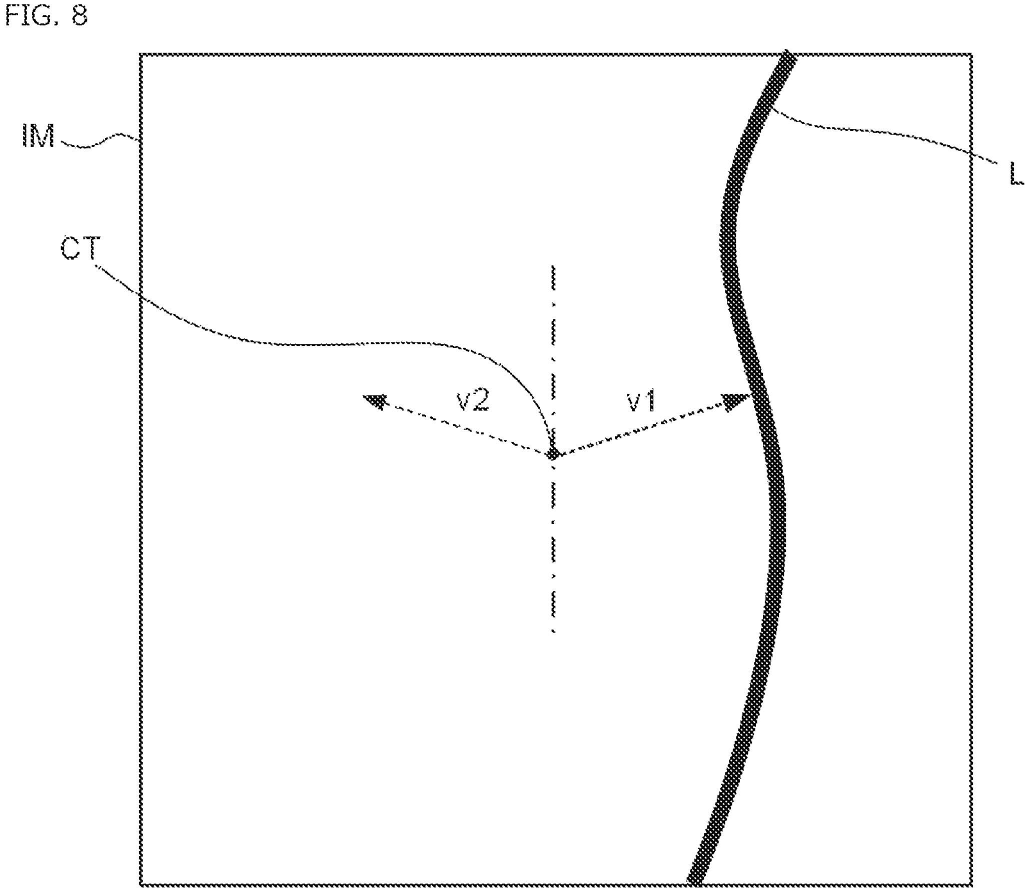
FIG. 8 is a schematic diagram representing an error vector v1.

Subsequently, the calculation unit 333 calculates the error vector v1 representing the error E between the target position TP (image center CT) and the line L (Activity A105). FIG. 8 is a schematic diagram representing the error vector v1. If the error E falls within the second range, which is a movable range of the position adjustment unit 44, the control signal generation unit 334 generates the control signal CS1 for correcting the error E and transmits to the position adjustment unit 44 (Activity A106). Furthermore, the control signal generation unit 334 generates the control signal CS2 for presenting the error E to the user U, and transmits to the error sense presentation unit 45 (Activity A107).

In other words, by transmitting the control signal CS1 to the position adjustment unit 44 in the main apparatus 4 via the communication unit 31, the position adjustment unit 44 drives, thereby the error E can be corrected. The control method in this case is not particularly limited, for example, P control, PD control, PID control, etc. may be employed as appropriate. Each coefficient related to control may be set to a preferred value as necessary. In addition, by transmitting the control signal CS2 to the error sense presentation unit 45 in the main apparatus 4 via the communication unit 31, the error sense presentation unit 45 operates, thereby the error E can be presented to the user U.

On the other hand, if the error E does not fall within the second range, which is the movable range of the position adjustment unit 44, the control signal generation unit 334 does not generate the control signal CS1 for correcting the error E, but generates the control signal CS2 for presenting the error E to the user U and transmit to the error sense presentation unit 45 (Activity A107).

The force sense or the tactile sense based on the error E is determined in proportion to the error vector v1 representing the error E. In other words, to present a magnitude (degree) and a direction of the error E to the user U, the force sense or the tactile sense may be imparted to the user U as a vector proportional to the error vector v1 (the proportionality constant is a positive or negative number, including 1). In particular, by imparting the force sense or the tactile sense to the left hand LH, which is different from the operating right hand RH, the error E can be presented to the user U without impairing sense of operation. In addition, especially preferably, the force sense or the tactile sense based on the error E is converted to a frequency suitable for human sensory presentation and presented. By presenting the force sense or the tactile sense at a frequency perceivable by human, the user U can grasp a state of the error E.

By repeating the control process described above in control rate units, the user U can train and learn a predetermined action. In summary, an operation method of the system 1 comprises: a first step of allowing the first limb HF1 of the user U to contact with the first contact unit 41 of the system 1, and allowing the second limb HF2 of the user U to contact with the second contact unit 42 of the system 1; a second step of allowing the target position TP defined by the operated portion 43 of the system 1 to move by moving the first limb HF1 that is in contact with the first contact unit 41; a third step of measuring the error E of the target position TP from a predetermined trajectory; and a fourth step of presenting the error E to the user U by imparting a force sense or a tactile sense based on the error E to the second limb HF2 that is in contact with the second contact unit 42.

3.2 Synchronized Motion

Supplementing the above assumption, the first limb HF1 and the second limb HF2 are preferably left and right hands (left hand LH and right hand RH) or left and right feet (left foot LF and right foot RF) of the user U. Human being realizes various and complicated task by using bilateral arm coordination. In order to move both human arms in a coordinated manner, it is thought that there is a brain mechanism that makes it possible to cooperate while being in the way. In particular, synchronized motion of both arms (e.g., both arms tend to move in the same way even if the right hand RH and the left hand LH try to perform different motions at the same time) are often observed in daily life, and synchronized control of both arms is considered to be the most fundamental mechanism for the brain.

In other words, when the force sense or the tactile sense is imparted to the left hand LH, the user U himself/herself quickly adjusts the right hand RH in a direction of correcting the error E by the synchronous motion of the left and right hands. According to such a control process, the user U can train and learn a predetermined action more intuitively and effectively regardless of age or motivation of the user U.

The force sense or the tactile sense based on the error E may be determined in proportion to the symmetric vector v2 obtained by symmetrically moving the error vector v1 representing the error E in relation to a symmetry plane (see FIG. 8). Here, the symmetry plane is a plane extending forward and backward from a trunk center of the user U. Considering stretching exercise or the like, human can naturally perform bilaterally symmetrical action using the plane extending forward and backward from the trunk center as the symmetry plane. Therefore, the user U may present the error E by force sense or tactile sense in proportion to the symmetry vector v2 instead of the error vector v1. Furthermore, it may be implemented in such a manner that the error vector v1 or the symmetry vector v2 can be selected according to preference of the user U.

4. Other

The system 1 may be further ingenuity by following aspects.

(1) The system 1 may further comprises an unshown guide light irradiation unit. The guide light irradiation unit may be coaxial with or fixed in a relative position to the imaging apparatus 2 (sensor unit), and may be configured to irradiate a guide light indicating the target position TP. Since a relative position of the guide light irradiation unit and the imaging apparatus 2 is known at the time of design, the target position TP can be irradiated as a projection light from the guide light irradiation unit. Preferably, the imaging apparatus 2 and the guide light irradiation unit may be implemented as a coaxial optical system using a beam splitter or the like. This allows the user U to more intuitively grasp how to move the first contact unit 41 so as to allow the target position TP to displace along the predetermined trajectory.

(2) In the aforementioned embodiment, although the target position TP is set as the intersection point (image center CT) of the line of sight of the imaging apparatus 2 and the regulation surface P, this is only an example and is not limited thereto. For instance, a cutting tool (e.g., end mill or medical scalpel) can be attached to the position adjustment unit 44 of the operated portion 43, and a tip position of the cutting tool can be set to the target position TP. In this case, a relative position of the imaging apparatus 2 and the cutting tool is known at the time of design. According to such a variation, the user U can perform training in cutting or medical treatment.

(3) Furthermore, a laser emission unit (for processing) can be attached to the position adjustment unit 44 of the operated portion 43, and an irradiation position (on the regulation surface P) of a laser emitted from the laser emission unit is set to the target position TP. In this case, a relative position of the imaging apparatus 2 and the laser emission unit is known at the time of design. According to such a variation, the user U can perform training of laser processing in such a manner that a desired object has a defined shape.

(4) Furthermore, an application unit configured to apply paint or the like can be attached to the position adjustment unit 44 of the operated portion 43, and a tip position of the application unit can be set to the target position TP. In this case, a relative position of the imaging apparatus 2 and the application tool is known at the time of design. According to such a variation, the user U can perform training of application process.

(5) Various objects can be considered as targets for determining the target position TP, including the cutting tool, the laser emission unit, the application tool, etc. mentioned above, and these can be implemented in such a manner that they can be freely attached and detached.

(6) Other sensor may be applied instead of or together with the imaging apparatus 2. For instance, a laser displacement sensor, an infrared sensor, or the like may be applied as appropriate.

(7) It may be implemented not as the system 1, but as a stand-alone control apparatus 3, which is a part of the system 1.

(8) A program may be implemented to allow a computer to function as the control apparatus 3.

Furthermore, the present invention may be provided in each of the following aspects.

The system, further comprising: a guide light irradiation unit coaxial with or fixed in a relative position to the sensor unit, and configured to irradiate a guide light indicating the target position.

The system, wherein: the first limb and the second limb are a left hand and a right hand of the user, and the first contact unit and the second contact unit are configured to be graspable by the left hand and the right hand, respectively.

The system, wherein: the force sense or the tactile sense based on the error is determined in proportion to an error vector representing the error.

The system, wherein: the first limb and the second limb are a left hand or foot and a right hand or foot of the user, and the force sense or the tactile sense based on the error is determined in proportion to a symmetric vector obtained by symmetrically moving the error vector representing the error in relation to a symmetry plane, wherein the symmetry plane is a plane extending forward and backward from a trunk center of the user.

The system, wherein: the force sense or the tactile sense based on the error is converted to a frequency suitable for human sensory presentation and presented.

The system, wherein: the sensor unit is an imaging unit configured to image information of an external world.

The system, wherein: the target position is a center of an image captured by the imaging unit.

The system, further comprising: a position adjustment unit configured to displace the operated portion within a second range that is smaller than a first range that can be operated by the user, and adjust a position of the operated portion so as to correct the error.

The system, wherein: an acquisition rate of the sensor unit and a drive rate of the position adjustment unit are 100 Hz or more.

An operation method of a system, comprising: a first step of allowing a first limb of a user to contact with a first contact unit of the system, and allowing a second limb of the user to contact with a second contact unit of the system; a second step of allowing a target position defined by an operated portion of the system to move by moving the first limb that is in contact with the first contact unit; a third step of measuring an error of the target position from a predetermined trajectory; and a fourth step of presenting the error to the user by imparting a force sense or a tactile sense based on the error to the second limb that is in contact with the second contact unit.

Of course, the above aspects are not intended to limit the present invention.

Finally, various embodiments of the present invention have been described, but these are presented as examples and are not intended to limit the scope of the invention. The novel embodiment can be implemented in various other forms, and various omissions, replacements, and changes can be made without departing from the abstract of the invention. The embodiment and its modifications are included in the scope and abstract of the invention and are included in the scope of the invention described in the claims and the equivalent scope thereof.

What is claimed is:

1. A system, comprising:

a main device configured to be operated by a first limb of a user, the main device being configured with at least a first contact unit and an operated component, the first contact unit connecting to the operated component, and configured to change a target position defined by the operated component within a first range, which is an operable range by a movement of the first limb of the user, in accordance with the movement of the first limb of the user by contacting the operated component with the first limb, the first limb being located at one of a right side and a left side of the user, wherein the operated component is directly displaced by the movement of the first limb of the user such that a displacement of the first limb continuously and proportionally corresponds to a displacement of the operated component;

a sensor unit configured to measure an error from a predetermined trajectory of the target position with respect to an actual trajectory due to the movement of the first limb;

a second contact unit including an error sense presentation unit, and configured to contact a second limb of the user, the second limb being located at the other of the right side and the left side of the user; and a position adjustment unit configured to displace the operated component within a second range that is smaller than the first range, and adjust a position of the operated component so as to correct the error without perceptibly altering a tactile sensation experienced by the first limb of the user when the error is within the second range, wherein the error sense presentation unit is configured to present the error to the user by imparting a force sensation or a tactile sensation, which is generated based on the error, to the second limb.

2. The system according to claim 1, further comprising:

a guide light irradiation unit coaxial with or fixed in a relative position to the sensor unit, the guide light irradiation unit being configured to irradiate a guide light indicating the target position.

3. The system according to claim 1, wherein:

the first limb and the second limb are a left hand and a right hand of the user, respectively, and the first contact unit and the second contact unit are configured to be graspable by the left hand and the right hand, respectively.

4. The system according to claim 1, wherein:

the force sensation or the tactile sensation, which is generated based on the error, is determined in proportion to an error vector representing the error.

5. The system according to claim 4, wherein:

the force sensation or the tactile sensation, which is generated based on the error, is converted to a frequency suitable for human sensory presentation, wherein the force sensation or the tactile sensation as the converted frequency is output.

6. The system according to claim 1, wherein:

the first limb and the second limb are a left hand or feet and a right hand or feet of the user, respectively, and the force sensation or the tactile sensation, which is generated based on the error, is determined in proportion to a symmetric vector obtained by symmetrically moving an error vector representing the error in relation to a symmetry plane, wherein the symmetry plane is a plane extending forward and backward from a trunk center of the user.

7. The system according to claim 1, wherein:

the sensor unit is an imaging unit configured to image information of an external world.

8. The system according to claim 7, wherein:

the target position is a center of an image captured by the imaging unit.

9. The system according to claim 1, wherein:

each of an acquisition rate of the sensor unit and a drive rate of the position adjustment unit is 100 Hz or more.

* * * * *